US007059717B2

(12) United States Patent
Bloch

(10) Patent No.: US 7,059,717 B2
(45) Date of Patent: Jun. 13, 2006

(54) EYEGLASSES WITH INTERCHANGABLE TEMPLE-MEMBERS

(76) Inventor: Nigel K. Bloch, PM Box-412, 991-C Lomas SanteFe Dr., Solana Beach, CA (US) 92075

( * ) Notice: Subject to any disclaimer, the term of this patent is extended or adjusted under 35 U.S.C. 154(b) by 0 days.

(21) Appl. No.: 10/916,180

(22) Filed: Aug. 10, 2004

(65) Prior Publication Data
US 2005/0036103 A1    Feb. 17, 2005

Related U.S. Application Data

(60) Provisional application No. 60/493,728, filed on Aug. 11, 2003.

(51) Int. Cl.
*G02C 5/14* (2006.01)

(52) U.S. Cl. ........................ 351/119; 121/156
(58) Field of Classification Search ........ 351/111–121, 351/140, 142, 149–152, 156–158; 2/448, 2/450, 452
See application file for complete search history.

(56) References Cited

U.S. PATENT DOCUMENTS

| 766,413 A | 8/1904 | Bloch | 351/116 |
|---|---|---|---|
| 3,118,962 A | 1/1964 | Hammond | 351/118 |
| 5,007,728 A | 4/1991 | Magorien | 351/118 |
| 5,511,251 A * | 4/1996 | Brakas | 2/452 |
| 5,594,511 A | 1/1997 | Lin | 351/116 |
| 5,781,273 A * | 7/1998 | Boden | 351/156 |
| 5,987,652 A * | 11/1999 | Fowler | 2/424 |
| 6,834,952 B1 * | 12/2004 | Polovin | 351/116 |
| 6,865,753 B1 * | 3/2005 | Nishida | 2/426 |

* cited by examiner

Primary Examiner—Huy Mai

(57) ABSTRACT

An eyeglasses apparatus and transformation system thereof, facilitating quick and easy convertibility of the left and right traditionally folding temples into an adjustable headband; thereby making the light-weight eyeglasses much more suited to dynamic activities such as jogging, skiing, and cycling for example. The user of this novel eyeware can advantageously move between more sedentary situations, where the extreme appearance of eye-goggles would appear very out of place;—yet by manually releasing an inconspicuously integrated pair of bifurcated retention-latches located immediately aftward of both temple-hinges, the temples can be instantly detatched and readily interchanged with a headband employing similar slide-in bayonet-type retention-latches. The disclosure identifies a particularly critical human-factors problem addressed by the uniquely configured finger operated opposed latches; plus, the notion of my slim-lined detatchable-temples, enables a host of optional companion accessory temple embodiments, facilitating a miniature radio, cell-phone, or digital-camera;—conveniences for the person on the go!

6 Claims, 1 Drawing Sheet

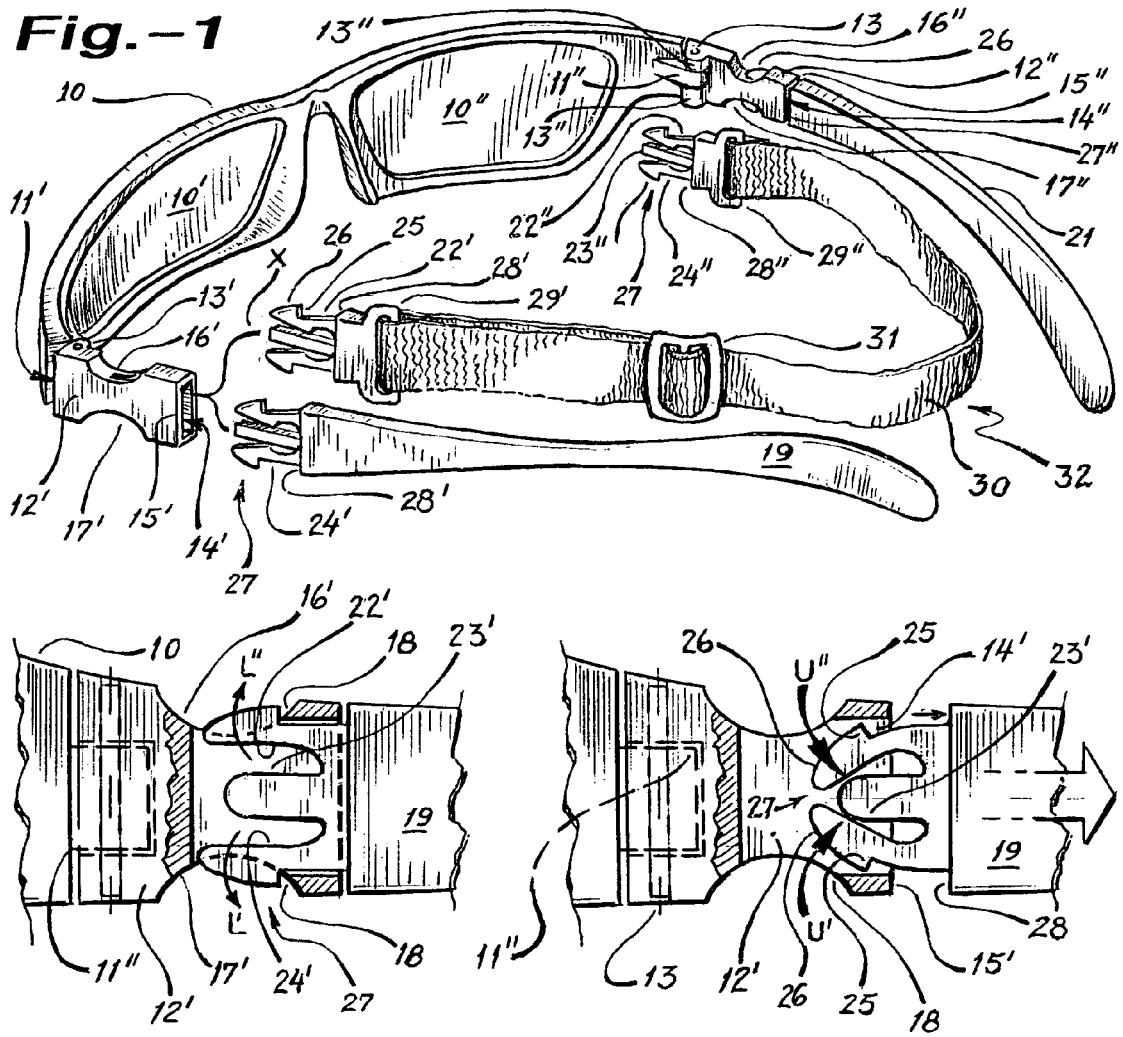
Fig.-1
Fig.-2A Fig.-2B
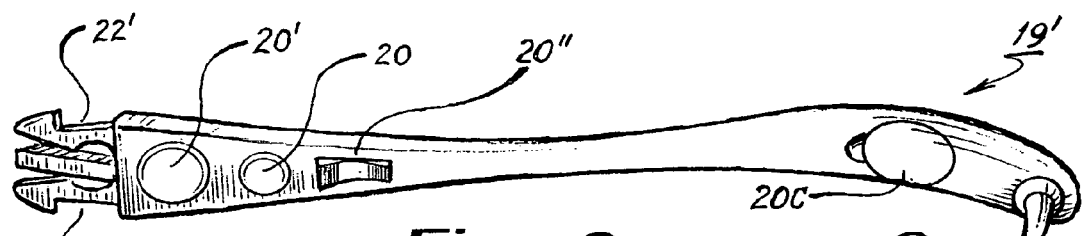
Fig.-3
Fig.-4

EYEGLASSES WITH INTERCHANGABLE TEMPLE-MEMBERS

This application claims the benefit of Provisional Application No. 60/493,728, filed Aug. 11, 2003.

BACKGROUND OF THE INVENTION

1. Field of the Invention

This disclosure relates to paired-eyeglasses or spectacles of the type having folding right and left temples supported upon users ears; and more specifically it relates to eyeware having some manner of conveniently detatchable and possibly interchangeable temple supporting members.

2. Relevant Prior-Art

Background research discovery provides some prior patent-art regarded as germane to this disclosure, chronologically for example, U.S. Pat. No. 766,413 (filed: August 1903) contemplates the notion of spectacles(pair of eyeglasses) having detachable left and right contemplates the notion of spectacles(pair of eyeglasses) having detachable left and right side temple support-arms by means of a fixed C-shaped receiver-mount which opposed C-lugs portions are employed to receive a the springy Y-shaped forward-tips at both the left and right temple/support-arms;—which afford a folding-hinge and appear to be readily detachable from the C-lugs when desired.

In U.S. Pat. No. 3,118,962 (filed: February 1961) is shown a pair of eyeglasses having abbreviated left and right conventionally hinging (for folding purposes) male/receiver-mounts, each having a plural-detented trailing-rod member which fits into a hole provided in the forward-end of both left and right temple/support-arms which male-ends thus insert into a medial/support-sleeve permanently attached over their respective male/receiver-mounts;—whereby a spring-loaded detenting-ball facilitates a convenient selective manual fore/aft-adjustment of their respective temple/support-arms (not intended to be completely detachable).

In U.S. Pat. No. 3,133,141 (filed: January 1962) is shown a pair of eyeglasses having slidingly adjustable aftward temple/support-arm members, which however are not actually intended to provide a detachable function.

In U.S. Pat. No. 3,394,980 (filed: June 1964) is shown a pair of eyeglasses having folding left and right temple/support-arms, and including plural trunion hinging points arranged along the temple/support-arms at spaced apart intervals; which however are not actually intended to provide a detachable function.

In U.S. Pat. No. 3,416,858) filed: March 1965) is shown a pair of eyeglasses having left and right temple/support-arms made in two optional generic variants, the first version showing the temple/support-arms being of a male-body configuration slidably fitting into the trailing-end of a hinging female/receiver-mount, the second version showing the temple/support-arms being of a female-body configuration slidably fitting around the hinging male/receiver-mount;—both iterations relying solely upon the friction-fit of the internally sliding portion as to achieve a variable adjustable length. Additionally, an optional hearing-aid fitted temple/support-arm is also set forth.

In U.S. Pat. No. 3,667,834 (filed: March 1971) is shown a pair of eyeglasses having left and right extended-trailing female/temple-supports, both sides including a forward support-swivel portion hingingly adapted to their respective conventional temple-support members; and in combination with left and right male male/support-arm members which thus slide within their respective female/temple-support portions. The aftward male/support-arm members each include a bifurcated-prong having laterally disposed accurately formed index-tip, which detents into one of plural indexing-detents provided in the sidewall of the female/temple-supports;—thereby enabling user to manually slideably adjust the aft male/support-arms to a suitable length relative to their ears, however the male/support-arm members are not intended to be detachable.

In U.S. Pat. No. 4,488,792 (filed: December 1984) is shown a pair of eyeglasses having detachable left and right temple/support-arms, wherein generic-variant removable wire-clip equipped hinge-pins are disclosed, which are said to enable the left and right temple/support-arms to be readily detached for the reason of obtaining a more intimate fitting and sealing when donning a military/gas-mask.

In U.S. Pat. No. 5,007,728 (filed: December 1989) is shown a pair of eyeglasses with conventional left and right temple-supports, to which hinges are adapted special left and right male/receiver-mounts having bifurcated-prongs, both upper prongs being a latching-prong having a positive-catch (24) formed thereto;—while both detachable temple/support-arms include a non-adjustable forward female/prong-receptacle having an internal cavity-separator partition (48/52) which cooperates with the lower/slider-prong (30), plus an engagement-relief (54) having a notch-catch (56),—whereby manual finger-tip depressing of the upper/latching-prongs obtains detachment so as to thereby change to differently styled temple/support-arms. These hollow-cavity temple/support-arms are necessarily rather costly to produce via two relatively complex three-piece injection-molding dies.

In U.S. Pat. No. 5,594,511 (filed: November 1995) is shown a pair of eyeglasses having left and right extended-trailing female/temple-supports, both sides including a forward support-swivel portion hingingly adapted to their respective conventional temple-mounting members; and in combination with left and right detachable male male/support-arm members which thus slidably engage into their respective female/temple-support portions. The male-prong of the aftward support-arm members each include a laterally disposed latch (503) which positively detents into a catch (400) formed integrally within the sidewall of the female/temple-supports;—thereby enabling user to manually remove the aft male/support-arms and substitute alternate male/head-strap members.

In U.S. Pat. No. 6,582,075 (filed: October 2001) is shown a pair of eyeglasses having left and temple/support-arms, which can be readily detached by removal of a special retention-pin at both left and right sides which features an annular-detent for engagement by a detent-spring at the temple/supports. The retention-pins also include discrete plural annular electrical-conductors, said useful in communicating of electrical-circuits between the left and right temple/support-arms. However, in actual practice it has been found that handling of such small retention-pins is not practical, as they are easily dropped and lost by the average user.

Therefore, in full consideration of the preceding patent review, there is determined a need for an improved form of device to which these patents have been largely addressed. The instant inventor hereof believes their newly improved eyeglasses invention, commercially referred to as the EQS™ (Eyeglasses Quick-release System), currently being developed for production under auspices of the Products-Mfg./Mkt.Co., exhibits certain advantages as shall be revealed in the subsequent portion of this instant disclosure.

SUMMARY OF THE INVENTION

A.) In view of the foregoing discussion about the earlier invention art, it is therefore important to make it pellucid to others interested in the art that the object of this invention is to provide a pair of convertible eyeglasses, or spectacles as they are also called, having substantially conventional left and right hinging portions to which are adapted special aftwardly extending left and right female/receiver-mounts, thereby accommodating readily detachable left and right temple/support-arm members. Note that to best facilitate this "convertibility"—objective, it was found advantageously practical to not employ the usual mirror-image left and right female/receiver-mount members. Instead, it was found that these two permanent non-detaching female/receiver-mounts could be molded from a common injection-molding die, and the same part is merely flipped-over 180-degreed left-to-right,—thereby enabling substantial cost-saving by sharing a common molding-die cavity. They employ a hollow tunnel-like female "support-cavity" portion which is relatively costly to injection-mold, owing that they involve a more complex three-piece molding-die (not shown in this disclosure because it is a conventional molding procedure). Additionally, the cooperatively detachable left and right extending mirror-image shaped male temple/support-arm members, can also be more economically produced from a less costly conventional longitudinally-split two-piece opposed-cavity injection-molding die. Hence, the point being made here is that the more costly components preferably remain a permanent part of my eyeglasses, while the detachable portions are less-costly, thereby enabling users of these eyeglasses to at any time enjoy purchasing variously styled modularly interchangable temple-supports (as to shape/size/color/trimmings, as well as my differently functioning temple/support-arms options),—on a very cost-effective basis.

B.) Another object of this invention disclosure is to set forth a pair of convertible eyeglasses having left and right female/receiver-mounts hingingly adapted to conventional fixed left and right temple-supports according to item-A, wherein the cooperative left and right male temple/support-arms are discretely detachable, both of the temple/support-arms having an upper and lower forward male latching-prong with outwardly-opposed catches upon their forwardmost terminuses. These trailing temple/support-arms are manually inserted forward into into their respective left or right trailing female/receiver-mount support-cavities, whereby the temple/support-arm latching-prong catches preferably being of a resilient-plastic thus upon moderate manual urging, snap into positive engagement with mating upper and lower engangement-reliefs formed integrally within both female/receiver-mount support-cavities. The discrete left and right temple/support-arms are therefore held fast into their respective left and right female/receiver-mount support-cavities, yet are readily detachable by a simple secondary detaching procedure, whereby the user need merely squeeze their thumb and opposing forefinger together at the opposite upper and lower engangement-reliefs formed into both of the female/receiver-mounts;— whereby of a critical improvement nature, the upper and lower latching-prongs yield and deflect against a preferred third or medial-prong of the male/pronged-assembly acts as a centering abutment deflection-limit member, assuring simultaneous disengagement of the opposed catches, whereupon the temple/support-arms are simply manually withdrawn.

In any case, even if the preferred medial-prong is not included as a part of the male/pronged-assembly, an upper/finger-relief and an opposed lower/finger-relief are nevertheless provided upon the discrete left and right said female/receiver-mounts proximal the upper and lower latching-catches, whereby simultaneous manual squeezing of one's thumb and an opposing finger at the upper/finger-relief and the lower/finger-relief (ie: finger above and thumb-below, or, thumb above and finger below), thus biases the latching-prongs toward one another as to thereby disengage the latching-catches from impingement upon said latching-notches, thus releasing the temple/support-arms free from retention by the female/receiver-mount.

C.) Another object of this invention disclosure is to set forth a pair of convertible eyeglasses having left and right female/receiver-mounts hingingly adapted to conventional fixed left and right temple-supports according to items-A&B, whereby in one regard the left and right detachable temple/support-arms can be fashioned into various aesthetic colorations and reconfigurations as design-trends may warrant. Additionally, although this disclosure essentially only sets forth information deemed pertinent to the specific utility function of detaching/attaching of either left or right temple/support-arms in a modular manner, it is to be understood that as such, the disclosed temple/support-arm apparatus may include optionally integrated accessory pomponents according to engineering design choice to provide an additional convenience-feature option,—such as an Am/Fm-radio, video-camera, cell-phone, and the like (all of which necessarily relying upon conventional state-of-art micro/integrated-circuiting);—hence, the novel detachable means being set forth herein thus serves to conveniently facilitate optional interchangability of temple/support-arms having substantially self-contained electronic operatives as well.

DESCRIPTION OF THE PREFERRED EMBODIMENT DRAWINGS

The foregoing and still other objects of this invention will become fully apparent, along with various advantages and features of novelty residing in the present embodiments, from study of the following description of the variant generic species embodiments and study of the ensuing description of these embodiments. Wherein indicia of reference are shown to match related matter stated in the text, as well as the Claims section annexed hereto; and accordingly, a better understanding of the invention and the variant uses is intended, by reference to the drawings, which are considered as primarily exemplary and not to be therefore construed as restrictive in nature; wherein:

FIG. 1, is a pictorial perspective-view, favoring the upper-left aftward portion of an exemplified pair of eyeglasses, wherein the trailing left temple/support-arm member is shown immediately detached from the forward left female/receiver-mount member,—and also shown thereto is an optionally interchangable temple/headband member;

FIG. 2A, is the first of two companion sequences showing an exemplified partial cross-sectional cut-away detail of the temple/support-arm, here revealing relationship of the latching-prongs during their normal positive full-engagement during use of the eyeglasses;

FIG. 2B, is the second of two sequences corresponding to FIG. 2A, here show only initially inserted as to reveal the vital relationship of the latching-prongs to the medial-prong during their normal detaching/attaching procedure;

FIG. 3, is a pictorial view showing an exemplified optional radio integrated within the left temple/support-arm;

FIG. 4, is a pictorial view showing an exemplified optional video-camera integrated within the left temple/support-arm.

ITEMIZED NOMENCLATURE REFERENCES 10,10'/10"—conventional binocular-frame, conventional Lenses: left/right
11',11"—conventional left/temple-support, conventional right/temple-support
12'/12"—female/receiver-mount: left/right
13,13'/13"—support-swivel pin, support-swivel: left/right
14'/14"—support-cavity: left/right
15'/15"—cavity-abutment: left/right
16'/16"—upper/finger-relief: left/right
17'/17"—lower/finger-relief: left/right
18—latching-notch (all four places)
19,19',19"—left temple/support-arm options: standard, radio-arm, videocam-arm
20,20',20"—component options: off/on-button, tuning-button, audio-volume rocker-switch
20C,20E,20M,20P,20V—bat.-cover, earphone, microphone, download-port, videocam
21—right temple/support-arm: standard
22'/22"—upper male/latching-prong: left/right
23'/23"—male medial-prong: left/right
24'/24"—lower male/latching-prong: left/right
25—latching-catch (all four places)
26—entry-ramp (all four places)
27—male/pronged-assembly
28'/28"—latching-abutment: left/right
29'/29"—male-extension/support-loop: left/right
30—headstrap
31—strap/adjustment-buckle
32—temple/strap-assembly
L'/L"—resilient-bias to expanded "Latched" condition
U'/U"—resilient-bias to convenged "Unlatched" condition
X—{—indicator representing interchangability

DETAILED DESCRIPTION OF THE PREFERRED EMBODIMENTS

Initial reference is given by way of FIG. 1, wherein is exhibited a pictorial view of my eyeglasses looking toward their backside so as to clearly reveal the novel construction of my detachable left temple/support-arm 19 and detachable right temple/support-arm 21, here the right temple/support-arm 21 being shown fully attached, as also would actually be the left,—during normal wear by the user. However, here the left standard temple/support-arm 19 is shown fully detached, as to thereby clearly reveal how detaching the standard left 19 and right 21 temple/support-arms, enables quick and easy insertion of attendantly shown alternate temple/strap-assembly 32. The abbreviated male-extension/support-loop portions 29'(left) and 29"(right) are supporting the oppositely affixed preferably elastic flexible head-band strap 30 member, preferably including a conventional adjustable strap/adjustment-buckle 31. This easily interchanged temple/strap-assembly 32 thus makes the otherwise rather traditional appearing eyeglasses readily convertible into a sport goggle; whereby the light-traveler can thus transform their eyeglasses into an embodiment much more suitable for activities such as skiing, skydiving, or swimming for example,—simply stowing the alternate components (ie: temple/strap-assembly 32 or temple/support-arms 19/21) conveniently in ones shirt-pocket if desired, whereby one is ready for any eventuality.

Therefore, regardless as to their configuration aftward of the left 28' and right 28" latching-abutments, the forwardly extending left and right male/pronged-assemblies 27 employ the same preferably tri-pronged configuration dependent from said left 28' and right 28" latching-abutment portions;—therefore characterizing a modular construction facilitating instant inter-changability of my different aftwardly extending temple-support options. Moreover, it is preferred that the male/pronged-assemblies 27 dependent from the left latching-abutment 28' and the right latching-abutment 28", are also capable of being conveniently interchangeable left to right (and hence right to left);—thereby in particular enabling the rigid left and right temple/support-arm assemblies 19 and 21 respectively to be optionally symmetrically configured for convenient support upon users either ear (a flip-over feature which is only really relevant in the case of the electronically adapted embodiments 19' and 19" to be discussed later herein).

There remain subtle, however vital other differences which are to become herein more evident and understood as important improvements. For example, FIGS. 2A/2B reveal vital details as to how the uniquely configured elements of the male/pronged-assembly 27 necessarily interact so as to engage with either supporting cavity-abutments 15' and 15" in a simultaneously biasing albeit oppositely latching manner. In FIG. 2B is shown how, as the male/pronged-assembly is manually urged into the support-cavity 14', the two opposed entry-ramps 26 of the upper 22' and lower 24' resilient-fingers have yielded in toward male/medial-prong member 23', and as the upper 22' and lower 24' resilient-fingers proceeded into the support-cavity 14' the centered male/medial-prong member 23' serves to limit the yielding convergence of the upper 22' and lower 24' resilient-fingers. Whilst in companion FIG. 2A is shown how the upper 22' and lower 24' resilient-fingers have sprung back out to their natural substantially relaxed condition once slidingly leaving the confines of support-cavity 14', whereby their upper and lower latching-catchs 25 positively engage against respective upper and lower latching-notchs 18,—thereby preventing withdrawal of the temple/support-arm 19. Conversely, to detach the temple/support-arm 19, the user simply squeezes their thumb and fore-finger together at both the upper/finger-relief 16' and lower/finger-relief 17', whereby the simultaneous convergence of both the upper male/latching-prong 22' and lower male/latching-prong 24' is caused to critically abut the male medial-prong 23';—thereby assuring a critical "balanced" simultaneous disengagement of both latching-catches 25, resulting in a non-snagging free-withdrawal of the male/pronged-assembly from support-cavity 14'. Therefore, it is critical to understand that without presence of the novel male medial-prong 23' member, it was found that a user could quickly became confounded when either the upper or lower latching-catch 25 would usually remain engaged;—at which point the frustrated user would commense to very forcibly yank at the temple/support-arm, ultimately leading to breakage of the temple-support structure 11' for example. Accordingly, it has been found that employment of the exemplified three-element male/pronged-assembly 27 on all of the exemplified interchangeable accouterments 19, 19', 19", 32,—assures a consistently smooth detachment procedure.

Reference to FIGS. 3 & 4 shows how my conveniently detachable temple/support-arms 19, can be readily interchanged with still other uniquely configured temple/support-arms 19' or 19" for example. The embodiment of FIG. 3 featuring an integral AM/FM-radio, having a conventional On/Off-button 20, a conventional sequentially operating PPL-type station-selecting tuning-button 20' coupled internally to a conventional integrated-circuit amplifier (unshown), a conventional audio-volume rocker-switch 20", a substantially conventional audio-transducer earphone 20E, and a system activating conventional button-battery (not shown) beneath battery-cover 20C. This aggregation defines a self-contained radio apparatus, not requiring external power-supply. The embodiment of FIG. 4 features an integral conventional videocam(ie: digital-camera) 20V with conventional On/Off-button 20, a conventional mini-microphone 20M, and optional conventional button-battery (unshown) power-supply 20C in the form of a female-receptacle 20P which function is akin to that of a conventional computer USB-port for subsequent downloading of pictures from a conventional internal microprocessor (unshown) to a conventional computer. This aggregation thus defining a digital-camera which can compile a series of individual snap-shot pictures, or process rapid-frame sequences tantamount to a video. Although the objective-lens is exemplified as situated at 20V, it can be arranged further forward if wide-angle images are desired. Therefore, while the basic objective is to provide the user of my EQS™-eyeglasses (ref. FIG. 1) with the convenience of readily interchanging between traditional appearing temple/support-arms 19 and 21, to a more sport-activity type of eyeglasses by readily substituting the temple/strap-assembly 32;—a further object of my versatile eyeglasses is to explore the full potential of interchangability as is set forth in the interchangeable electronics-equipped temple/support-arms of FIGS. 3 and 4.

Thus, it is readily understood how the preferred and generic-variant embodiments of this invention contemplate performing functions in a novel way not heretofore available nor realized. It is implicit that the utility of the foregoing adaptations of this invention are not necessarily dependent upon any prevailing invention patent; and, while the present invention has been well described hereinbefore by way of certain illustrated embodiments, it is to be expected that various changes, alterations, rearrangements, and obvious modifications may be resorted to by those skilled in the art to which it relates, without substantially departing from the implied spirit and scope of the instant invention. Therefore, the invention has been disclosed herein by way of example, and not as imposed limitation, while the appended Claims set out the scope of the invention sought, and are to be construed as broadly as the terminology therein employed permits, reckoning that the invention verily comprehends every use of which it is susceptible. Accordingly, the embodiments of the invention in which an exclusive property or proprietary privilege is claimed, are defined as follows.

What is claimed is:

1. A pair of convertible eyeglasses comprising:
    a left female mounting member permanently and hingedly attached to a left side of said eyeglasses, said left female mounting member having an opening and a support cavity through said opening, said left female mounting member further having an upper notch and a lower notch in communication with said support cavity;
    a right female mounting member permanently and hingedly attached to a right side of said eyeglasses said right female mounting member having an opening and a support cavity through said opening, said right female mounting member further having an upper notch and a lower notch in communication with said support cavity;
    a left temple support arm having an upper and a lower male latching prong, said left temple support arm removably insertable into said support cavity whereby said upper and lower male latching prongs engage in and are retained respectively by said upper and lower notches; and
    a right temple support arm having an upper and a lower male latching prong, said right temple support arm removably insertable into said support cavity whereby said upper and lower male latching prongs engage in and are retained respectively by said upper and lower notches;
    whereby pinching the upper and lower male latching prongs toward one another and down into the support cavity disengages the upper and lower male latching prongs respectively from said upper and lower notches to permit removal of either said right temple support arm or said left temple support arm, or both, from said eyeglasses.

2. The convertible eyeglasses according to claim 1, wherein said left and right temple support arms include a medial-prong member acting as a centering abutment against which said upper and lower male latching prongs become ultimately biased during the manual release procedure, said medial-prong member thereby eliminating any tendency of said upper and lower male latching prongs to otherwise snag upon each other.

3. The convertible eyeglasses according to claim 1, wherein pinching action upon said upper and lower male latching prongs is ultimately balanced by provision of a medial-prong disposed equidistant there between, whereby said upper and lower male latching prongs are thus biased evenly away from each other thereby obviating otherwise tendency of snagging on each other.

4. The convertible eyeglasses according to claim 1, wherein said left and right temple support arms are readily interchangeable in a modular manner with a temple strap assembly having an abbreviated body terminating with a male extension having a headstrap thereby obviating possibility of improper mounting.

5. The convertible eyeglasses according to claim 1 further comprising a radiocam in either said right temple support arm or in said left temple support arm or in both.

6. The convertible eyeglasses according to claim 1 further comprising a videocam in either said right temple support arm or in said left temple support arm or in both.

* * * * *